United States Patent [19]
Goldstein

[11] Patent Number: 4,932,420
[45] Date of Patent: Jun. 12, 1990

[54] NON-INVASIVE QUARTER WAVELENGTH MICROWAVE APPLICATOR FOR HYPERTHERMIA TREATMENT

[75] Inventor: Kenneth Goldstein, Plano, Tex.

[73] Assignee: Clini-Therm Corporation, Dallas, Tex.

[21] Appl. No.: 255,115

[22] Filed: Oct. 7, 1988

[51] Int. Cl.$^5$ .............................................. A61N 5/00
[52] U.S. Cl. ..................................... 128/804; 128/783; 128/401; 128/399; 343/700 MS
[58] Field of Search ............... 128/399, 401, 783, 798, 128/804; 343/700 MS

[56] References Cited

U.S. PATENT DOCUMENTS

| | | | |
|---|---|---|---|
| 4,190,053 | 2/1980 | Sterzer | 128/399 |
| 4,397,313 | 8/1983 | Vaguine | 128/399 |
| 4,397,314 | 8/1983 | Vaguine | 128/399 |
| 4,446,874 | 5/1984 | Vaguine | 128/804 |
| 4,471,787 | 9/1984 | Bentall | 128/804 |
| 4,589,423 | 5/1986 | Turner | 128/804 |
| 4,633,262 | 12/1986 | Traut | 343/700 MS |
| 4,660,048 | 4/1987 | Doyle | 343/700 MS |
| 4,812,855 | 3/1989 | Coe et al. | 343/700 MS |

FOREIGN PATENT DOCUMENTS

| | | | |
|---|---|---|---|
| 1498885 | 3/1969 | Fed. Rep. of Germany | 128/804 |
| 1228872 | 5/1986 | U.S.S.R. | 128/804 |

OTHER PUBLICATIONS

"Microstrip Loop Radiators for Local Hyperthermia", Bahl et al., IEEE MTT Symposium (LA), Jun. 1987.
"A Microstrip Antenna for Medical Applications", Bahl et al., IEEE MTT Symposium (DC), May 1980.
"A New Microstrip Radiation for Medical Applications", Bahl et al., IEEE-MTT 28, vol. 12, 12-1980.

*Primary Examiner*—Edward M. Coven
*Assistant Examiner*—Jessica Harrison
*Attorney, Agent, or Firm*—Richards, Medlock & Andrews

[57] ABSTRACT

A printed circuit board structure fabricated to define a plurality of quarter wavelength microstrip antennas, each radiating microwave energy in a dipole pattern. The ends of the microstrip antennas are formed overlapping the ends of adjacent microstrip antennas so that a resultant additive effect of the radiated microwave energy is exhibited near the ends of the antennas. The overall effect is to produce a more uniform radiation pattern which does not have the typical radiation minima located at the ends of the dipole antennas.

26 Claims, 2 Drawing Sheets

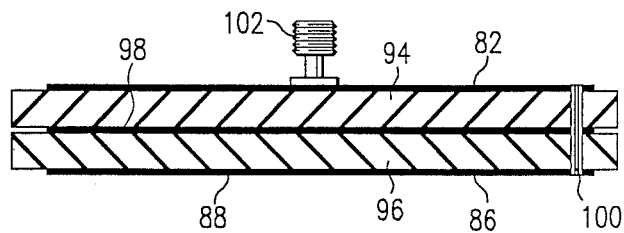
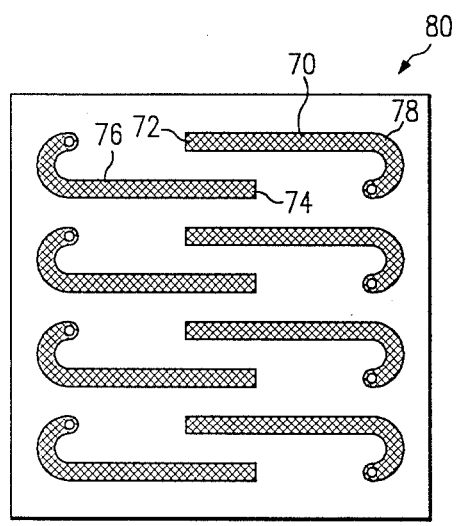
FIG. 4
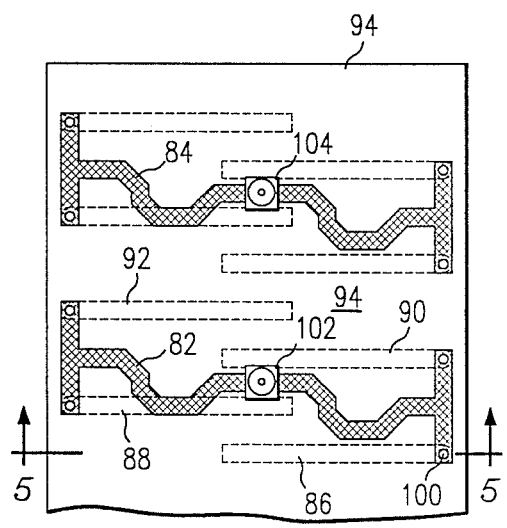
FIG. 5
FIG. 6
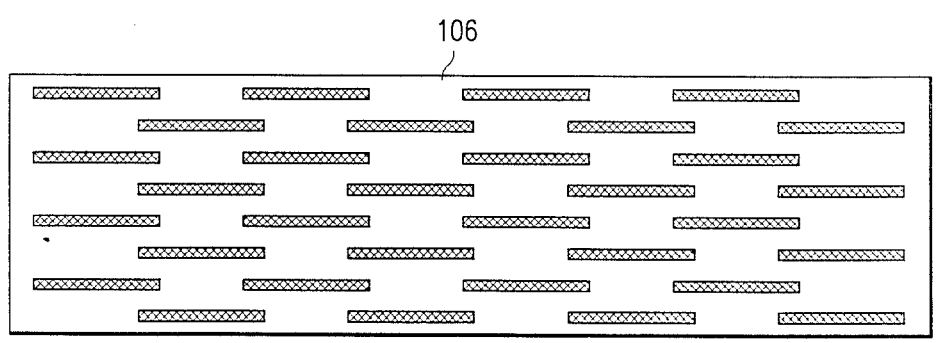
FIG. 7

NON-INVASIVE QUARTER WAVELENGTH MICROWAVE APPLICATOR FOR HYPERTHERMIA TREATMENT

FIELD OF THE INVENTION

The present invention relates in general to methods and apparatus for treating malignant tissues using hyperthermia techniques, and more particularly relates to a non-invasive microwave applicator having plural quarter wavelength microstrip antennas for producing uniform heating of the subsurface malignant tissue.

BACKGROUND OF THE INVENTION

Hyperthermia is a relatively new area in the medical sciences for treating subsurface cancerous or malignant tissues, such as tumors. It has become well known that the destruction of such cancerous tissues can be accelerated by elevating the temperature thereof to about 43° C. When the malignant tissue is elevated to such temperature for a period of time, for example, an hour, the malignant cells are weakened and are eventually destroyed. Hyperthermia treatment is generally carried out in conjunction with radiation treatments to destroy malignant tissues, especially those in which the tissue is in a relatively well defined area below the surface of the skin.

The mechanism which allows the cancerous tissues to be destroyed, without destroying normal surrounding tissue, is that the malignant tissue is generally characterized by poor blood circulation with reduced oxygen. The microwave energy induced within the tumorous tissue heats the tissue to such an extent that the limited blood circulation cannot dissipate the heat. This contrasts with normal healthy surrounding tissue having sufficient blood circulation which readily carries the microwave-generated heat away. For a better understanding of hyperthermia treatment techniques and apparatus, reference is made to U.S. Pat. Nos. 4,397,313; 4,397,314 and 4,446,874, all assigned to Clini-Therm Corporation, Dallas, Tex.

While there exists many different techniques for elevating the temperature of subsurface malignant tissues, a common concern attendant with all such techniques is that of the uniform heating of the tissue to assure that the well-defined temperature of 43° C. is achieved throughout the malignant tissue. In other words, in many microwave application techniques where the heat distribution, or temperature gradient, within the malignant tissue is non-uniform, hot spots and cool spots will occur, thereby reducing the effectiveness of the treatment.

Microwave applicators utilized for the hyperthermia treatment of tissue include interstitial antennas which are inserted into the malignant tissue. A plurality of such antennas, generally being of a quarter wavelength with respect to the transmitting frequency, are inserted into the patient in a matrix pattern in an attempt to achieve uniform heating. Not only is this painful to the patient, but also the lateral dipole radiation is accompanied with cool spots which exist between the dipole radiation patterns. Cavity or waveguide type microwave applicators held against the skin of a person are not an invasive type of applicator, but are heavy and bulky and require special apparatus for holding against the patient during the long periods of microwave application. More recently, there has been developed printed microstrip circuit boards with a pattern of antennas, each about 10-14 wavelengths long. This latter approach is reported to be effective, but can cover only a small portion of the surface area of the applicator. Thus, additional robotics equipment is utilized to continuously move the small microstrip applicator about the surface of the tumor so that over a period of time the entire malignant tissue is heated to the desired temperature. It is apparent that in utilizing this approach a higher instantaneous power is required to achieve the desired temperature of the malignant tissue.

From the foregoing, it can be seen that a need exists for a new microwave application technique, and corresponding apparatus, for providing a non-invasive and highly uniform application of microwave energy to a subsurface malignant tissue. An additional need exists for microwave energy applicators which are lightweight and easily constructed with different surface areas to accommodate different sizes of malignant tumors. Yet another need exists for a microwave applicator which can be utilized with currently available microwave transmitters, and which requires no additional skill on the part of the personnel administering the hyperthermia treatment.

SUMMARY OF THE INVENTION

In accordance with the present invention, the disclosed non-invasive microwave applicator substantially reduces or eliminates the disadvantages and shortcomings associated with the prior art techniques. According to the invention, the microwave applicator is constructed with a number of quarter wavelength microstrip antennas arranged in a geometric pattern to achieve uniform energy radiation therefrom, and thus a uniform heating distribution within a malignant tissue.

According to the preferred embodiment of the invention, the microwave applicator includes a printed circuit board base structure having a plurality of quarter wavelength microstrip antennas separated from a conductive backplane by an insulating dielectric. The energy radiation pattern of each quarter wavelength microstrip antenna is hemispherical, with an energy radiation maxima near the center of each antenna and a minima near the ends thereof. The microstrip antennas are arranged in parallel rows with the ends of each antenna overlapping the ends of other similar antennas in adjacent rows. With this arrangement, the additive effect of the radiated minima near the antenna ends results in an energy level which is substantially similar in magnitude to the radiation maxima existing at the center of the microstrip antennas. An overall uniform distribution of radiated energy is thereby achieved over the entire surface of the applicator which, when applied adjacent to a tissue area to be treated, also induces a uniform level of heat energy therein.

A technical advantage of the invention as a result of the arrangement of overlapping microstrip antennas is a uniform heating of a malignant tissue so that the temperature therein is uniformly elevated throughout the bulk of the tissue, whereby a more reliable and effective treatment of the malignant tissue is achieved.

The microstrip antennas located near opposing edges of the applicator can be formed in a semicircular configuration to achieve an overlapping arrangement and thus an additive effect of the radiated energy near the edges of the applicator.

While each microstrip antenna can be driven by a separate microwave energy source, a group of microstrip antennas can be connected together at ends thereof and driven by a single microwave energy source. A multilayer printed circuit board provides an ideal base for the quarter wavelength microstrip applicator which is easily constructed, lightweight and reliable. A top conductive layer of the multilayer printed circuit board is etched to define a serpentine connection strip to connect desired ones of the microstrip antennas together for driving the group by a single microwave energy source. A bottom conductive layer of the multilayer printed circuit board is etched to define the microstrip antennas. An inner conductive layer defines the ground plane for the antennas and is separated from the upper and lower patterned conductive layers by first and second dielectric layers. Plated through holes in the circuit board are effective to connect the ends of the quarter wavelength antennas to the serpentine connection strip. A microwave connector is fixed to the connection strip so that a transmitter can drive all antennas in a group in a coherent manner. A cover and an associated attachment bracket are fixed to the printed circuit board base to provide a mechanism for fixing to other apparatus so that the applicator can be held stationary and adjacent to the area of a patient to be treated.

BRIEF DESCRIPTION OF THE DRAWINGS

Further features and advantages will become apparent from the following and more particular description of the preferred embodiment of the invention, as illustrated in the accompanying drawings in which like reference characters generally refer to the same parts or elements throughout the views, and in which:

FIG. 4 illustrates a pattern of microstrip antennas having semicircular shaped ends to produce an additive effect of the radiated energy adjacent the edges of the applicator;

FIG. 5 illustrates a multilayer printed circuit board adapted for connecting plural microstrip antennas together for driving by single microwave energy source;

FIG. 6 is a top view of the multilayer structure of FIG. 5; and

FIG. 7 illustrates a large number of overlapped quarter wavelength antennas for providing a large area microwave applicator.

DETAILED DESCRIPTION

Figure 1:
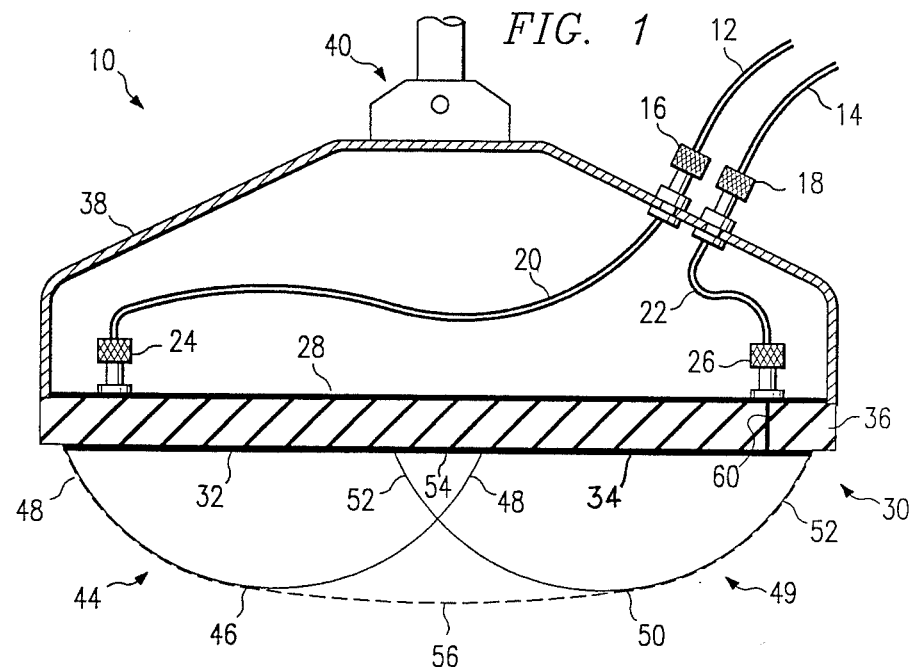
FIG. 1 is a sectional view of microwave hyperthermia treatment applicator, constructed in accordance with preferred embodiment of the invention.

Shown in FIG. 1 is a sectional view of a microwave applicator constructed in accordance with the preferred embodiment of the invention. While the disclosed embodiments of the applicator may be suitable for use in a variety of applications, the invention is particularly well suited for hyperthermia treatment applications. In such an application, the applicator, generally designated by reference character 10, and a water-filled bolus (not shown) are placed adjacent the skin area of the patient over an underlying malignant tissue area. The water bolus is placed between the applicator 10 and the patient to maintain the normal tissue of the patient at a body temperature or about 37° C.

Microwave energy is then applied to the applicator 10 via one or more electrical coaxial conductors 12 and 14, through electrical connectors 16 and 18 and intermediate shielded conductors 20 and 2 to yet other internal electrical connectors 24 and 26. The body of the connectors 24 and 26 are fixed, such as by soldering, to a grounded backplane 28 of a printed circuit board 30. The internal conductor of the connectors 24 and 26 are connected through the printed circuit board 30 to quarter wavelength microstrip antennas 32 and 34, and perhaps others, which are formed on the bottom side of the circuit board. The microstrip antennas 32 and 34 are separated from the conductive backplane 28 by an insulating dielectric 36. A protective cover 38 is shown fixed to the printed circuit board 30 to provide protection to the components therein, and well as to provide a frame structure for fastening a bracket 40 thereto so that other equipment can be fastened to the applicator 10 for holding it adjacent to the desired area of the patient.

In operation, when microwave energy, preferably of about 915 mhz, is applied to coaxial conductor 12, the microstrip antenna 32 radiates energy in a pattern shown by reference character 44. The radiated pattern 44 is similar to that of a dipole, including a maxima 46 near the center of the microstrip antenna 32 and minima 48 near the ends of the antenna 32. The application of microwave energy to microstrip antenna 34, via coaxial conductor 14, produces a similar radiation pattern 49 with maxima and minima radiation energy at respective locations 50 and 52. The microwave energy utilized for driving the microstrip antennas 32 and 34 is coherent, e.g., in phase. In accordance with an important feature of the invention, the microstrip antennas 32 and 34 overlap at a central minima location 54 such that the minima radiation at locations 48 and 52 are additive to produce a resultant radiated energy pattern at location 56. The broken line indicated by reference numeral 56 indicates the resultant radiation pattern generated by the applicator 10 of the invention. As can be appreciated, a more uniform energy pattern is radiated which results in a more uniform heating of the desired tissue of the patent.

Figure 2:
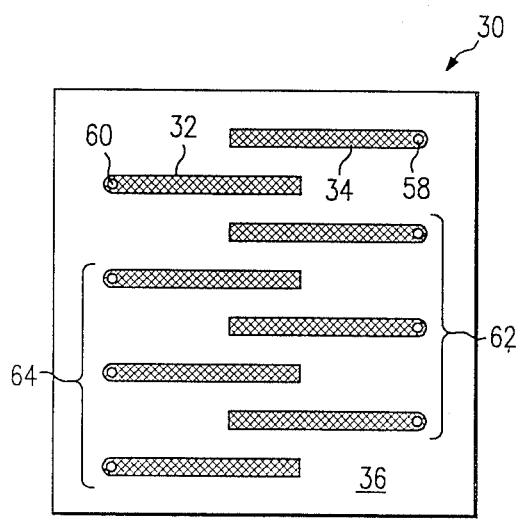
FIG. 2 is a bottom view of the applicator, illustrating the microstrip antennas arranged in an overlapping manner.

The configuration of an array of microstrip antennas of the applicator 10 is shown in detail in FIG. 2. Particularly shown is the bottom of the printed circuit board 30 with a first column of microstrip antennas, such as 32, and a second column, such as 34. Each antenna is end fed, as noted by the feed through connections at the end of each antenna. As can be seen, an end section of antenna 32 overlaps with that of antenna 34 to produce an additive effect of the radiation minima occurring at such locations of the antenna. Indeed, the other microstrip antennas formed on the circuit board 30 are similarly constructed and arranged to produce an aiding or additive effect at the locations in which a quarter wavelength dipole antenna normally produces a minimum radiation. As a result, a majority of the area of the circuit board 30 produces a microwave radiation pattern which is more uniform than would be achieved if the antennas were not overlapping at the locations noted. The microstrip antennas 32 and 34, as well as the others noted in FIG. 2, are conductive and end fed with microwave energy by way of the printed circuit board feed through connections, such as shown by reference character 60 (FIG. 1).

In the preferred form of the invention, microwave energy of about 915 mhz is applied to the various microstrip antennas formed on the circuit board 30. With such a driving energy frequency, the microstrip antennas are quarter wavelength long, or about 5.0 cm (2.0 inches). In order to provide proper impedance matching between the quarter wavelength antenna array and the underlying water bolus and tissue of the patient, the microstrips are constructed with a line width of about 0.3175 cm (0.125 inches). In order to produce a resultant uniform radiating pattern, the extent by which the microstrip antennas are overlapped is about 20%-25of the length of the antennas, or about 1 cm (0.40 inches) at 915 mhz. The thickness of the material from which each microstrip antenna is constructed is rather arbitrary, but is sufficiently thick to accommodate the power of the microwave driving source.

In the preferred embodiment of the invention, the transmitter is characterized by a 50 ohm output impedance, and thus all other transmission lines, circuits, connectors and antennas are also fabricated to exhibit a 50 ohm impedance to the microwave energy. Hence, the system is impedance matched throughout to reduce reflected energy and thus to transfer substantially all the energy to the tissue of the patient.

The printed circuit board 30 from which the quarter wavelength microstrip antenna array of the invention is formed may be of conventional construction, including opposing copper clad surfaces sandwiched about a high dielectric Teflon bonded fiberglass material. The dielectric constant $\epsilon$ is about 2.32. The characteristic impedance microstrip structures constructed with such printed circuit board materials is:

$$Z_o = \frac{377h}{\sqrt{\epsilon_r} \times W \left[1 + 1.735\epsilon_r^{-.0724}\left(\frac{W}{h}\right)^{-.836}\right]}$$

where $\epsilon_r$ is the dielectric constant,
W is the width of the line,
h is the height of the dielectric.

Figure 3:
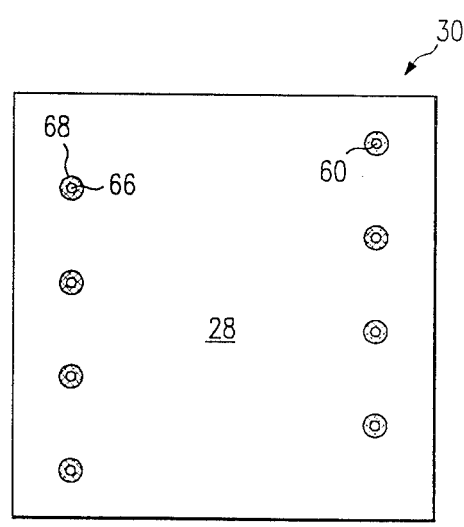
FIG. 3 is a top view of the printed circuit board base of FIG. 2.

One side of the circuit board is masked and patterned in a conventional manner to define the configuration of the microstrip antenna array, and etched to remove the copper material in the unpatterned areas. The other side of the printed circuit board may be similarly etched to define the feed through hole areas in the backplane 28, as shown in FIG. 3. A majority of the surface of the printed circuit board 30 shown in FIG. 3 is covered with a ground conductor 28, preferably copper with solder reflowed thereover. Alternatively, the conductive antenna structures can be gold flashed, rather than reflow soldered, to provide a surface resistant to oxidation and corrosion. As noted above, the backplane conductor 28 operates in conjunction with the quarter wavelength microstrip antennas to produce the radiated energy patterns described above. As noted, the top side of the printed circuit board 30 is covered with a masking material and etched to form the isolated islands, such as 66. The isolated islands 66 are conductive, and in electrical contact with the plated through structures 68 which connect to the respective microstrip antennas located on the bottom side of the printed circuit board 30. The masking and etching steps in the construction of the plated through structures are carried out using well known techniques.

FIG. 4 illustrates another embodiment of the invention, in which a plurality of quarter wavelength microstrip antennas are formed, again with overlapping ends, but with other semicircular end structures located near opposing ends of the circuit board 80. Particularly shown is a microstrip antenna 70 having an end 72 overlapping with end 74 of an adjacent microstrip antenna 76. Each microstrip antenna includes a semicircular end 78 which produces a radiation field, the additive effect of which increases the microwave power emitted near the opposing edges of the printed circuit board 80. As a result, a substantially uniform microwave radiation pattern is emitted substantially over the entire area of the printed circuit board 80, thereby providing a better defined and uniform transmission pattern for heating a malignant tissue area of similar size.

FIGS. 5 and 6 illustrate yet another embodiment of the invention in which plural microstrip antennas are joined together and driven simultaneously from a single microwave source. Illustrated is a cross-sectional view of a multilayer printed circuit board structure according to such embodiment. An upper patterned conductive layer defines serpentine connection strips 82 and 84 which are routed along paths for connecting together plural quarter wavelength microstrip antennas, such as 86-92. The serpentine shape of the connection strips 82 and 84 effectively lengthen such strips to the proper wavelength so that the microwave transmitter is matched to the antennas and maximum power is delivered.

The microstrip antennas are formed by patterning a conductive layer on the bottom of the multilayer structure. The upper serpentine connection strip 82 is formed over a first dielectric layer 94. A second dielectric layer 96 defines a base on which the conductive material of the microstrip antennas are patterned and formed. The dielectric layers 94 and 96 are sandwiched to an inner conductive ground plane 98 which forms a plane for the radiation of the quarter wavelength antennas. A plated through connection 100 serves to connect microstrip antenna 86 to the common connection strip 82. The remaining microstrip antennas 88-92 are similarly connected through the multilayer printed circuit board by plated through connections to the common interconnection strip 82, or other similar strips. Of course, the plated through conductors 100 are not in electrical contact with the conductive ground plane 98.

A microwave connector 102 is soldered, or otherwise electrically fixed, to the common interconnection strip 82 for driving all four microstrip antennas 85-92 with a single microwave source. The microwave source will require four times the power which is normally required to drive a single microstrip antenna. In addition, those skilled in the art will realize that special precautions must be taken to match the impedance of the microwave energy source to the four microstrip antennas, which are shown connected in parallel. Such a design consideration is well within the ambit of those skilled in the art.

While not shown, an inner conductor of the connector 102 is connected to the common interconnection strip 82, while the base or case of the connector 102 is connected to the inner ground plane 98 via a plated through conductor (not shown). The embodiment illustrated in FIGS. 5 and 6 depicts the concept of the invention which can be extended to yet additional arrays of antennas and the parallel driving of antenna arrays numbering more or less than that shown.

Quarter wavelength antenna arrays with a large number of antennas, such as shown in FIG. 7, can be utilized to provide a large area for the hyperthermia treatment of a large malignant area. As can be seen from FIG. 7, the printed circuit board 106 is constructed with eight rows of quarter wavelength antennas, each with four antennas per row. As with the structures described above, the ends of each microstrip antenna are adjacent and overlap the ends of antennas in other rows to thereby provide a uniform and large area coverage for the microwave energy. While the printed circuit structure shown in FIGS. 7 is rectangular in shape, square printed circuit structures can be utilized with additional rows of microstrip antennas to provide yet a larger area of microwave radiation coverage. Also, those skilled in the art may find that in certain cases it may be expedient to fabricate the antenna structures of the invention by techniques other than with printed circuit board or microstrips. In applications it may also be advantageous to arrange the antennas in a nonparallel relationship, but yet with overlapping ends to produce the radiation summation described above.

From the foregoing, it can be seen that an improved hyperthermia treatment applicator is disclosed which substantially reduces or eliminates the shortcomings of the prior art structures. The selection of plural quarter wavelength antennas provides a well defined radiation pattern for generating heat within a malignant body tissue. In addition, by overlapping the ends of the quarter wavelength microstrip antennas, the traditional dipole radiating areas are enhanced, such that the additive effect near the ends of the antennas produces a resultant uniform energy distribution at predetermined distances from the planar bottom surface of the applicator. By employing the printed circuit board technology, the quarter wavelength antennas can be easily fabricated with current technology. Accordingly, the microwave applicator of the invention can be constructed at a low cost and provide a highly reliable device.

While the preferred and other embodiments of the invention have been disclosed with reference to specific microwave applicators, and methods of use and fabrication, it is to be understood that many changes in detail may be made as a matter of engineering choices without departing from the spirit and scope of the invention as defined by the appended claims.

What is claimed is:

1. A non-invasive microwave applicator for use in hyperthermia treatment, comprising:
    a generally planar base structure to which a microwave energy source is electrically coupled;
    a plurality of quarter wavelength antennas defining an array, said array being mechanically connected to said base and electrically connected to the microwave energy source to produce individual dipole radiation patterns, said antennas being arranged with respect to each other so that the dipole radiation minima of each said antenna is additive with the radiation minima of adjacent antennas such that an overall uniform radiation pattern is generated and transmitted outwardly orthogonally to said planar base structure to thereby provide an enhanced uniform heating of an area of treatment having about the same area as said array.

2. The microwave applicator of claim 1, wherein said antennas are arranged on said base structure in a parallel relationship, and the ends of ones of said antennas are adjacent the ends of other antennas so that the radiation emitted from the adjacent antenna ends is additive.

3. The microwave applicator of claim 1, wherein said base comprises a printed circuit board with a ground backplane, and said antennas comprise microstrips separated from said backplane by a dielectric material.

4. The microwave applicator of claim 1, wherein at least a longitudinal portion of ones of said antennas is linear.

5. The microwave applicator of claim 4, wherein said base structure includes peripheral edges with antennas arranged proximate said edge, and said antennas located near the edge of said base have curved ends to produce an increased microwave radiation adjacent side edges of said base due to additive radiation energy of said curved antenna ends.

6. The microwave applicator of claim 1, wherein said antennas are microstrip antennas arranged in rows in a spaced apart manner, with a longitudinal end section of said antennas being laterally adjacent with longitudinal end sections of other antennas in adjacent rows such that the electrical energy radiated by the adjacent end sections is additive.

7. The microwave applicator of claim 6, wherein a quarter wavelength of the ends of a majority of said antennas are adjacent with a quarter wavelength of the ends of different antennas on said base structure.

8. The microwave applicator of claim 1, wherein said antennas are end fed with coherent microwave energy.

9. The microwave applicator of claim 8, further including an interconnection strip for connecting a group of said antennas together for driving by one source of said microwave energy.

10. The microwave applicator of claim 9, wherein said base comprises a multilayer printed circuit board having said antennas insulated from said interconnection strips, and an insulated conductive ground plane.

11. The microwave applicator of claim 8, further including a microwave generator connected to said applicator for generating microwave energy at 915 mhz.

12. The microwave applicator of claim 1, wherein said antennas have ends overlapped with ends of other said antennas by about 20%–25% of the length of said antennas.

13. A non-invasive microwave applicator for use in hyperthermia treatment, comprising:
    a printed circuit board base having a ground plane separated by a dielectric layer from a plurality of quarter wavelength microstrip antennas driven by a microwave energy source, each said antenna having a longitudinal end section thereof which is laterally adjacent a longitudinal end section of another said microstrip antenna such that a radiation pattern generated at the adjacent ends of said antennas is additive and results in a summation which is substantially equal to the radiation magnitude existing in a longitudinal center part of each said microstrip antenna.

14. The microwave applicator of claim 13, wherein groups of said microstrip antennas are connected together for driving by a single microwave source.

15. The microwave applicator of claim 13, further including microwave generator means for driving all said microstrip antennas in a coherent phased relationship.

16. A non-invasive microwave applicator for use in hyperthermia treatment, comprising:
    a multilayer printed circuit board base having,
        an upper conductive pattern defining antenna interconnections,
        a first dielectric, an inner conductive plane,
a second dielectric, and
a bottom conductive pattern defining a plurality of antennas;
said upper conductive pattern being routed so as to overlie a plurality of said antennas;
feed through conductors electrically connecting said upper conductive pattern to said plurality of antennas; and
a connector connected to said upper conductive pattern for coupling a microwave energy source via said upper conductive pattern to said plurality of antennas.

17. The microwave applicator of claim 16, wherein said plurality of antennas defines a group, and further including a plurality of other similarly constructed groups of said antennas to define an array.

18. The microwave applicator of claim 16, wherein said inner conductive plane defines a ground plane, and further including a feed through conductor connecting said ground plane to said connector.

19. The microwave applicator of claim 16, wherein each said antenna has an end with a longitudinal portion adjacent a longitudinal portion of an end of another said antenna to produce an additive effect on the radiated energy of both said longitudinal end portions.

20. The microwave applicator of claim 19, wherein the longitudinal adjacency of said antennas comprises a length in the range of about 20%-25% of the entire length of each said antenna.

21. A method for generating a uniform microwave energy pattern for use in hyperthermia treatment applications, comprising the steps of:
arranging a plurality of microwave antennas to form an array on an applicator so that longitudinal end portions of ones of said antennas are adjacent with longitudinal end portions of other said antennas to produce an additive radiation of said adjacent end portions; and
coupling one or more sources of microwave energy to the antenna array so that a substantially uniform radiation pattern is achieved.

22. The method of claim 21, further including driving all said antennas with coherent energy sources.

23. The method of claim 21, further including forming said antenna array with quarter wavelength antennas, each of which radiate energy in a dipole pattern.

24. The method of claim 23, further including overlapping said antennas by about 20%-25% of the length thereof.

25. The method of claim 21, further including driving two or more of said antennas defining a group with a single energy source.

26. The method of claim 25, further including connecting each antenna of a group together for driving by said single energy source.

* * * * *